(12) United States Patent
Lee

(10) Patent No.: US 9,835,144 B2
(45) Date of Patent: Dec. 5, 2017

(54) ATOMIZER

(71) Applicant: Ming-Hsien Lee, Taichung (TW)

(72) Inventor: Wen Ching Lee, Taichung (TW)

(73) Assignee: Ming-Hsien Lee, Taichung (TW)

( * ) Notice: Subject to any disclaimer, the term of this patent is extended or adjusted under 35 U.S.C. 154(b) by 1023 days.

(21) Appl. No.: 14/108,601

(22) Filed: Dec. 17, 2013

(65) Prior Publication Data

US 2015/0139838 A1    May 21, 2015

(30) Foreign Application Priority Data

Nov. 18, 2013    (TW) .............................. 102141869 A

(51) Int. Cl.
  *F04B 1/02*      (2006.01)
  *A61M 11/02*   (2006.01)
  *A61M 11/06*   (2006.01)

(52) U.S. Cl.
  CPC ................ *F04B 1/02* (2013.01); *A61M 11/02* (2013.01); *A61M 11/06* (2013.01); *A61M 2205/07* (2013.01); *A61M 2210/0618* (2013.01)

(58) Field of Classification Search
  CPC .. A61M 11/042; A61M 11/005; A61M 11/06; A61M 2205/07; A61M 2210/0618; A61M 11/02; A61M 15/08; A61M 1/0037; F04B 1/02; F04B 27/005; F04B 27/02
  USPC .......................... 417/234, 254, 561, 415, 521
  See application file for complete search history.

(56) References Cited

U.S. PATENT DOCUMENTS

| | | | | |
|---|---|---|---|---|
| 6,193,475 B1 * | 2/2001 | Rozek | ..................... | F04B 35/04 417/360 |
| 6,648,612 B2 * | 11/2003 | Hsiao | .................. | F04B 39/0016 417/313 |
| 6,783,333 B2 * | 8/2004 | Wang | ...................... | F04B 35/01 417/307 |
| 7,240,642 B2 * | 7/2007 | Chou | .................... | F04B 39/123 123/41.35 |
| 8,079,824 B2 * | 12/2011 | Chou | ...................... | F04B 35/06 417/16 |
| 8,297,944 B2 * | 10/2012 | Chou | .................... | F04B 35/008 285/33 |
| 8,522,833 B2 * | 9/2013 | Chou | .................... | F04B 35/008 141/38 |
| 2010/0108185 A1 * | 5/2010 | Chou | ................... | B29C 73/166 141/38 |

* cited by examiner

*Primary Examiner* — Devon Kramer
*Assistant Examiner* — Lilya Pekarskaya
(74) *Attorney, Agent, or Firm* — Rosenberg, Klein & Lee

(57) ABSTRACT

An atomizer includes a motor mounted in a housing. First and second cylinder units are received in the housing. The first cylinder unit includes a first piston and a first coupling bearing connected to the first piston. The second cylinder unit includes a second piston and a second coupling bearing connected to the second piston. An eccentric transmission shaft of the motor extends through the first and second coupling bearings of the first and second cylinder units. The first and second pistons of the first and second cylinder units move reciprocatingly when the motor operates. An intake check valve is mounted in an intake passage between an intake port of the first cylinder unit and an inlet of the housing. An outlet check valve is mounted in an outlet passage between an outlet port of the second cylinder unit and an outlet of the housing.

4 Claims, 8 Drawing Sheets

ATOMIZER

BACKGROUND OF THE INVENTION

The present invention relates to an atomizer and, more particularly, to an atomizer including a plurality of cylinder units to separate an inlet from an outlet.

An atomizer generally includes a main body having an inlet or outlet for sucking, injecting, or atomization purposes. The atomizer can be used in medical treatments, such as medical care of nasal cavities and throats of patients in ear-nose-throat departments of hospitals and elderly healthcare centers. In an application of the sucking function, a nasal mucus sucker can be used with the main body of the atomizer to suck nasal mucus and accumulated phlegm out of the nasal cavity of a patient. In an application of the injecting function, an injector (or nasal spray) can be used with the main body to clean the nasal cavity, the throat or a wound of a patient. In another application of the injecting function, a sprayer can be used with the main body to proceed with spray treatment in the nasal cavity or throat.

In an arrangement, the main body of the atomizer includes a housing receiving a motor and a cylinder unit having an inlet and an outlet. A check valve is mounted in each of an inlet passage for the inlet and an outlet passage for the outlet of the cylinder unit, providing the cylinder unit with an intake function and an outtake function. Each of the inlet and the outlet is connected by a connection pipe to an exterior of the housing. Thus, the cylinder unit includes an inlet piping and an outlet piping. An outlet end of the inlet piping forms the inlet of the atomizer, and the outlet end of the outlet piping forms the outlet of the atomizer. The inlet piping is not in communication with the outlet piping under normal conditions. However, the check valves are generally flexible resilient members in which the inlet piping or the outlet piping is opened or closed upon flexing or not flexing of the resilient members. The check valves of this type are liable to fatigue after the atomizer has been used for a period of time. Thus, incomplete closing could occur though the inlet piping or the outlet piping should be closed, leading to undesired communication between the inlet piping and the outlet piping and causing risks of cross infection.

Thus, a need exists for a novel atomizer that mitigates and/or obviates the above disadvantages.

BRIEF SUMMARY OF THE INVENTION

An atomizer according to the present invention includes a housing having an inlet and an outlet. A motor is mounted in the housing and includes an eccentric transmission shaft. A first cylinder unit is mounted in the housing. The first cylinder unit includes a first piston and a first coupling bearing connected to the first piston. The eccentric transmission shaft extends through the first coupling bearing. The first piston moves reciprocatingly when the motor operates. The first cylinder unit further includes an intake port. An intake check valve is mounted in an intake passage for the intake port of the first cylinder unit. The intake port of the first cylinder unit is connected to an end of a first connection pipe. The other end of the first connection pipe is connected to the inlet of the housing, forming an intake piping for the first cylinder unit. A second cylinder unit is mounted in the housing. The second cylinder unit includes a second piston and a second coupling bearing connected to the second piston. The eccentric transmission shaft extends through the second coupling bearing. The second piston moves reciprocatingly when the motor operates. The second cylinder unit further includes an outlet port. An outlet check valve is mounted in an outlet passage for the outlet port of the second cylinder unit. The outlet port of the second cylinder unit is connected to an end of a second connection pipe. The other end of the second connection pipe is connected to the outlet of the housing, forming an outlet piping for the second cylinder unit.

In a form shown, the housing further includes a first vent and a second vent. The first cylinder unit further includes an outtake port. An outtake check valve is mounted in an outtake passage for the outtake port of the first cylinder unit. The outtake port of the first cylinder unit is connected to an end of a third connection pipe. The other end of the third connection pipe is connected to the first vent of the housing, forming an outtake piping for the first cylinder unit. The second cylinder unit further includes an inlet port. An inlet check valve is mounted in an inlet passage for the inlet port of the second cylinder unit. The inlet port of the second cylinder unit is connected to an end of a fourth connection pipe. The other end of the fourth connection pipe is connected to the second vent of the housing, forming an inlet piping for the second cylinder unit.

In the form shown, the motor further includes a mounting frame fixed to a side thereof. The first and second cylinder units are mounted to the mounting frame. The eccentric transmission shaft is located between the first and second cylinder units. The first and second cylinder units are spaced from each other by 180 degrees as viewed from a longitudinal axis of the eccentric transmission shaft.

In the form shown, each of the first and second cylinder units includes a cylinder body and a cover covering the cylinder body. The intake port and the outtake port of the first cylinder unit are located in the cover of the first cylinder unit. The inlet port and the outlet port of the second cylinder unit are located in the cover of the second cylinder unit.

In the form shown, the first cylinder unit further includes a spacer plate between the cylinder body and the cover of the first cylinder unit. The cylinder body of the first cylinder unit includes a top wall facing the cover of the first cylinder unit. The top wall includes an inlet opening and an outlet opening. The cover of the first cylinder unit includes an upper wall. A partitioning wall extends from the upper wall of the cover of the first cylinder unit toward the cylinder body of the first cylinder unit. The partitioning wall has a bottom face pressing against the spacer plate. The upper wall of the cover of the first cylinder unit, the partitioning wall, and the spacer plate divide an interior of the cover of the first cylinder unit into an inlet section and an outlet section not in communication with the inlet section. The inlet opening is in communication with the inlet section and the intake port of the cover of the first cylinder unit to form the intake passage of the first cylinder unit. The outlet opening is in communication with the outlet section and the outtake port of the cover of the first cylinder unit to form the outtake passage of the first cylinder unit.

In the form shown, the spacer plate includes a first punched hole aligned with the inlet opening of the cylinder body of the first cylinder unit. The spacer plate further includes a second punched hole aligned with the outlet opening of the cylinder body of the first cylinder unit. A remaining material in the first punched hole is connected to the spacer plate and forms the intake check valve of the first cylinder unit. A remaining material in the second punched hole is connected to the spacer plate and forms the outtake check valve of the first cylinder unit.

In the form shown, the cover of the first cylinder unit includes a hollow tube located in the inlet section and extending toward the cylinder body of the first cylinder unit. The hollow tube is in communication with the inlet section and the intake port of the first cylinder unit. The hollow tube has a bottom side pressing against the intake check valve of the first cylinder unit.

In the form shown, the inlet opening of the cylinder body of the first cylinder unit includes a first rib extending in a diametric direction. The first rib is spaced from the intake check valve of the first cylinder unit by a first spacing, providing room for the intake check valve. The intake check valve of the first cylinder unit has a free end capable of swinging toward the cylinder body of the first cylinder unit to open the intake passage of the first cylinder unit such that an intake effect is provided when the piston of the first cylinder unit reciprocates, In the form shown, the outlet opening of the first cylinder unit includes a second rib extending in a diametric direction. The second rib presses against the outtake check valve of the first cylinder unit. The outtake check valve of the first cylinder unit is spaced from the outlet section by a second spacing, providing room for the outtake check valve. The outtake check valve of the first cylinder unit has a free end capable of swinging toward the cover of the first cylinder unit such that an outtake effect is provided when the piston of the first cylinder unit reciprocates.

The present invention will become clearer in light of the following detailed description of illustrative embodiments of this invention described in connection with the drawings.

DETAILED DESCRIPTION OF THE INVENTION

Figure 1:
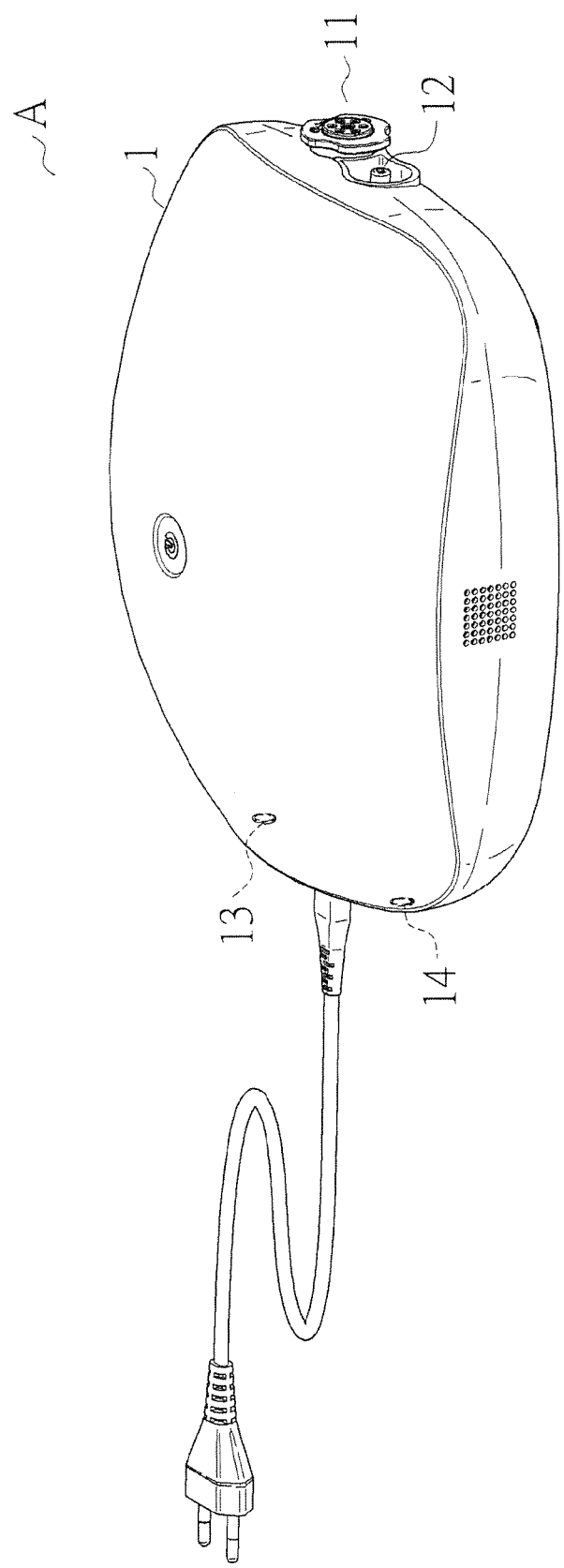
FIG. 1 is a perspective view of an atomizer according to the present invention.
Figure 2:
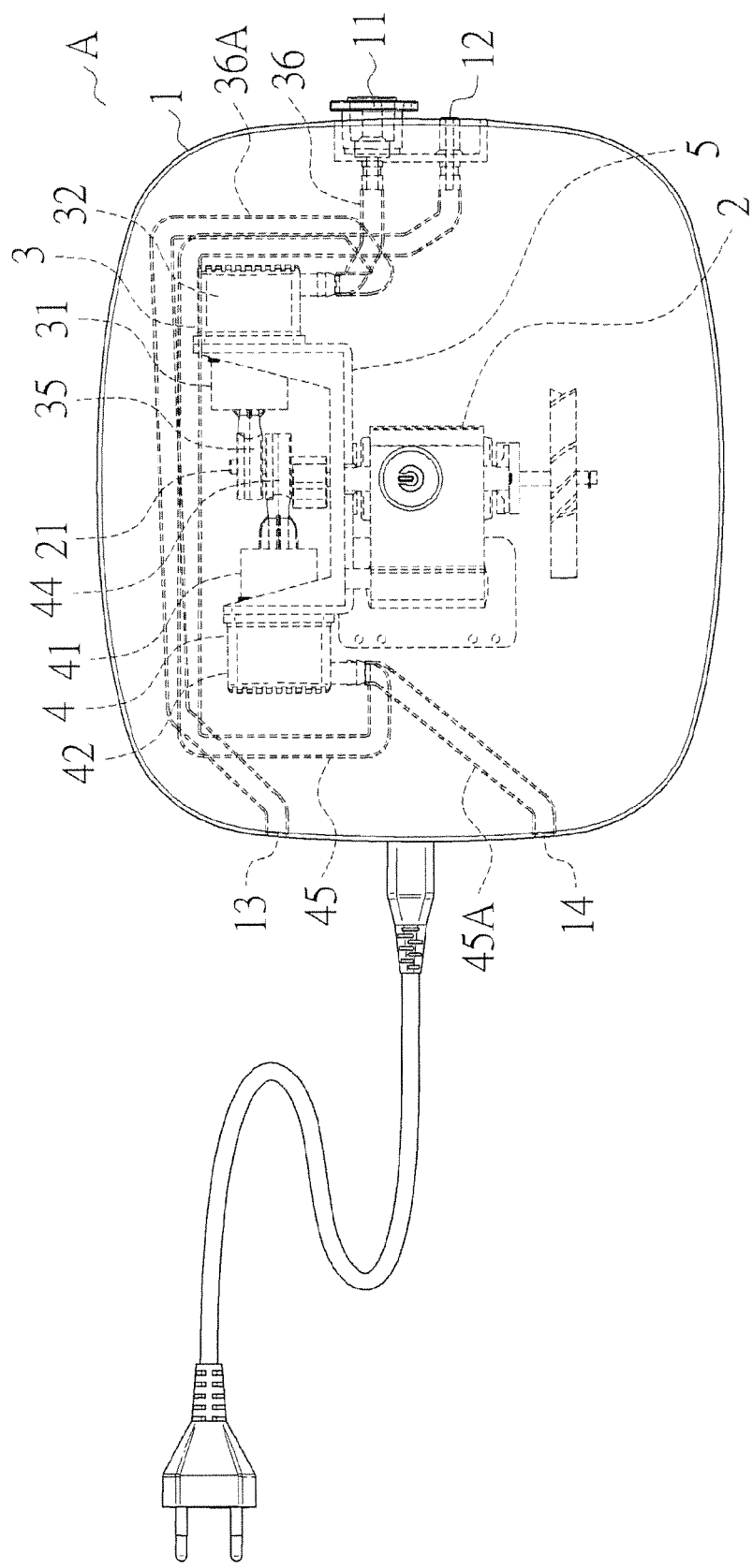
FIG. 2 is a top view of the atomizer of FIG. 1, with components of the atomizer shown with phantom lines.
Figure 3:
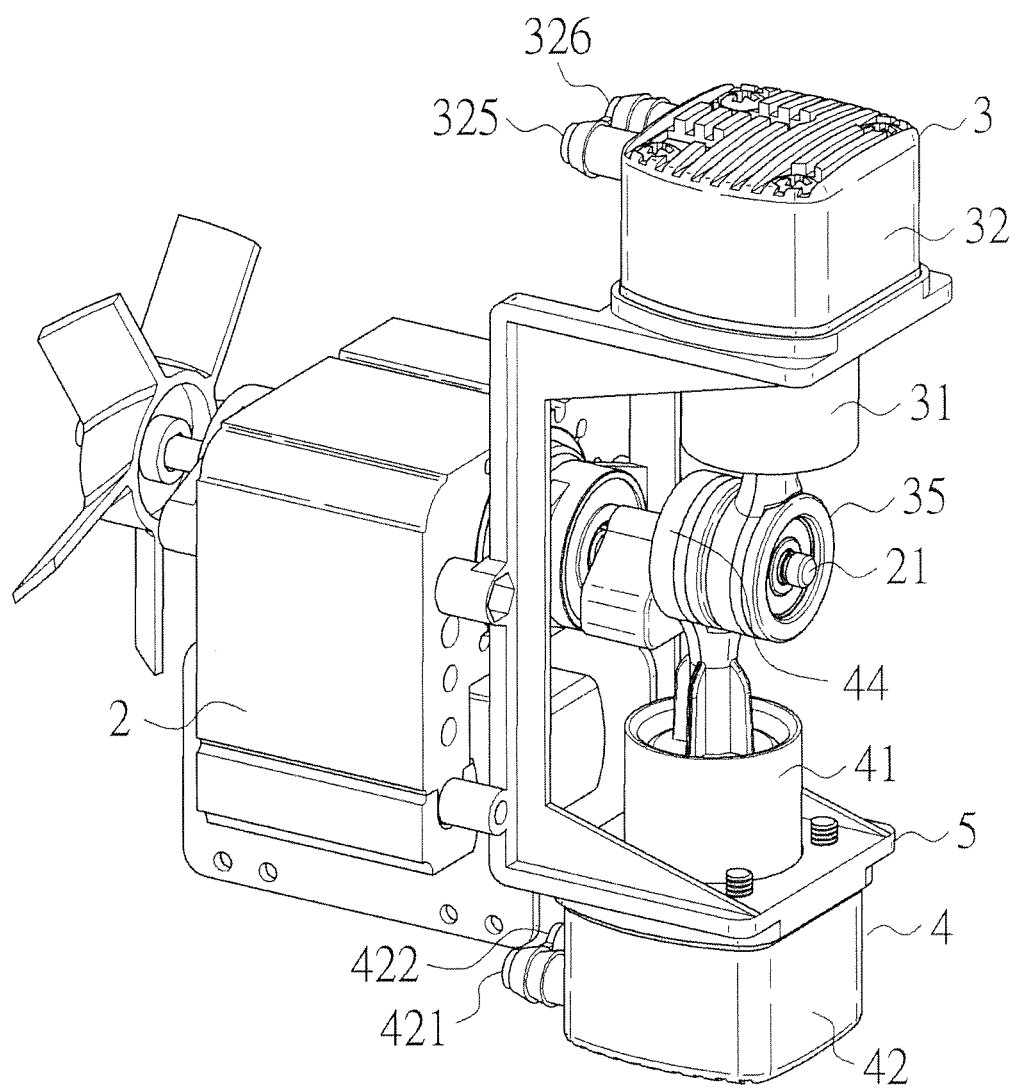
FIG. 3 is a perspective view of a dual cylinder structure of the atomizer of FIG. 1.

With reference to FIGS. 1-6, an atomizer A according to the present invention includes a housing 1 having an inlet 11 and an outlet 12. A motor 2 is mounted in the housing 1 and includes an eccentric transmission shaft 21. A first cylinder unit 3 is mounted in the housing 1 and includes a first piston 34 and a first coupling bearing 35 connected to the first piston 34. The eccentric transmission shaft 21 extends through the first coupling bearing 35. The first piston 34 moves reciprocatingly when the motor 2 operates. The first cylinder unit 3 further includes an intake port 325. An intake check valve 332 (FIG. 7) is mounted in an intake passage for the intake port 325 of the first cylinder unit 3. The intake port 325 of the first cylinder unit 3 is connected to an end of a first connection pipe 36. The other end of the first connection pipe 36 is connected to the inlet 11 of the housing 1, forming an intake piping for the first cylinder unit 3.

A second cylinder unit 4 is mounted in the housing 1 and includes a second piston 43 and a second coupling bearing 44 connected to the second piston 43. The eccentric transmission shaft 21 extends through the second coupling bearing 44. The second piston 43 moves reciprocatingly when the motor 2 operates. The second cylinder unit 4 further includes an outlet port 422. An outlet check valve (not shown) is mounted in an outlet passage for the outlet port 422 of the second cylinder unit 4. The outlet port 422 of the second cylinder unit 4 is connected to an end of a second connection pipe 45. The other end of the second connection pipe 45 is connected to the outlet 12 of the housing 1, forming an outlet piping for the second cylinder unit 4. Thus, the inlet 11 and the outlet 12 are respectively in communication with the first and second cylinder units 3 and 4 different from each other, avoiding cross infection.

In the form shown, the motor 2 further includes a mounting frame 5 fixed to a side thereof. The first and second cylinder units 3 and 4 are mounted to the mounting frame 5, with the eccentric transmission shaft 21 located between the first and second cylinder units 3 and 4. The First and second cylinder units 3 and 4 are spaced from each other by 180 degrees as viewed from a longitudinal axis of the eccentric transmission shall 21.

Since the first connection pipe 36 for the intake piping of the first cylinder unit 3 is connected to the inlet 11 of the housing 1 and since the second connection pipe 45 for the outlet piping of the second cylinder unit 4 is connected to the outlet 12 of the housing 1, the intake piping will not be in communication with the outlet piping even if fatigue of the intake check valve 332 and the outlet check valve (not shown) occur after a period of time of use, effectively avoiding cross infection during use. A nasal mucus sucker, injector (or nasal spray), sprayer, or breast pump can be connected to the inlet 11 or the outlet 12. Users of these devices can feel ease during use. Furthermore, since the first and second cylinders 3 and 4 are paced from each other by 180 degrees as viewed from the longitudinal axis of the eccentric transmission shaft 21, vibrations resulting from reciprocating movements of the cylinders 34 and 43 are counterbalanced by each other. Thus, the atomizer A operates more smoothly than atomizers having only one cylinder unit.

In the form shown, the housing 1 further includes a first vent 13 and a second vent 14. The first cylinder unit 3 further includes an outtake port 326. An outtake check valve 333 (FIG. 7) is mounted in an outtake passage for the outtake port 326 of the first cylinder unit 3. The outtake port 326 of the first cylinder unit 3 is connected to an end of a third connection pipe 36A. The other end of the third connection pipe 36A is connected to the first vent 13 of the housing 1, forming an outtake piping for the first cylinder unit 3. The second cylinder unit 4 further includes an inlet port 421. An inlet check valve (not shown) is mounted in an inlet passage for the inlet port 421 of the second cylinder unit 4. The inlet port 421 of the second cylinder unit 4 is connected to an end of a fourth connection pipe 45A. The other end of the fourth connection pipe 45A is connected to the second vent 14 of the housing 1, forming an inlet piping for the second cylinder unit 4. The first and second vents 13 and 14 allow more smooth operations of the first and second cylinder units 3 and 4. Furthermore, the first and second vents 13 and 14 will not be connected to the nasal mucus sucker, injector (or nasal spray), sprayer, or breast pump, avoiding cross infection. Thus, the users of these devices can feel ease during use.

Figure 4:
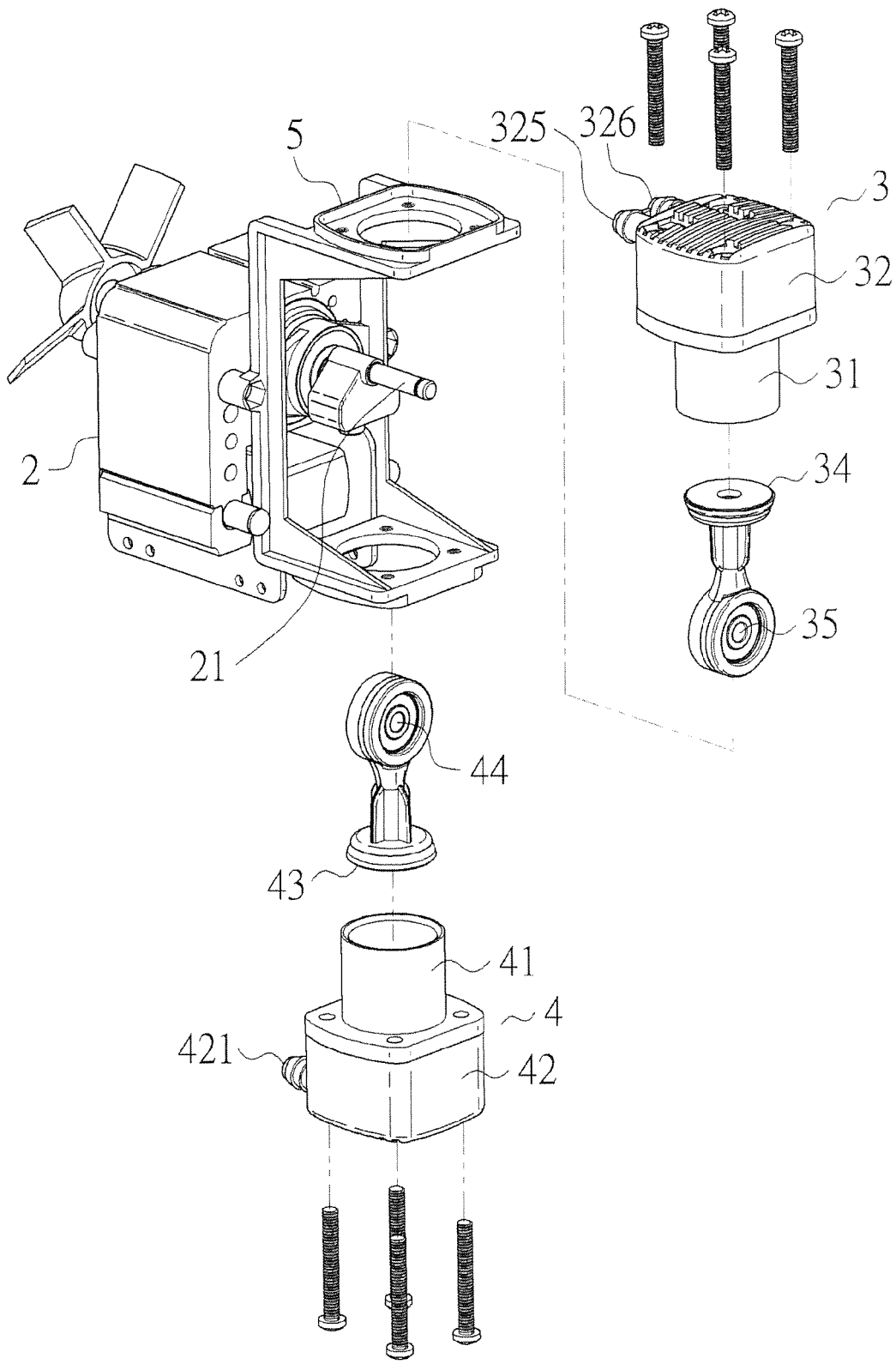
FIG. 4 is a perspective view of the dual cylinder structure of the atomizer of FIG. 3.
Figure 5:
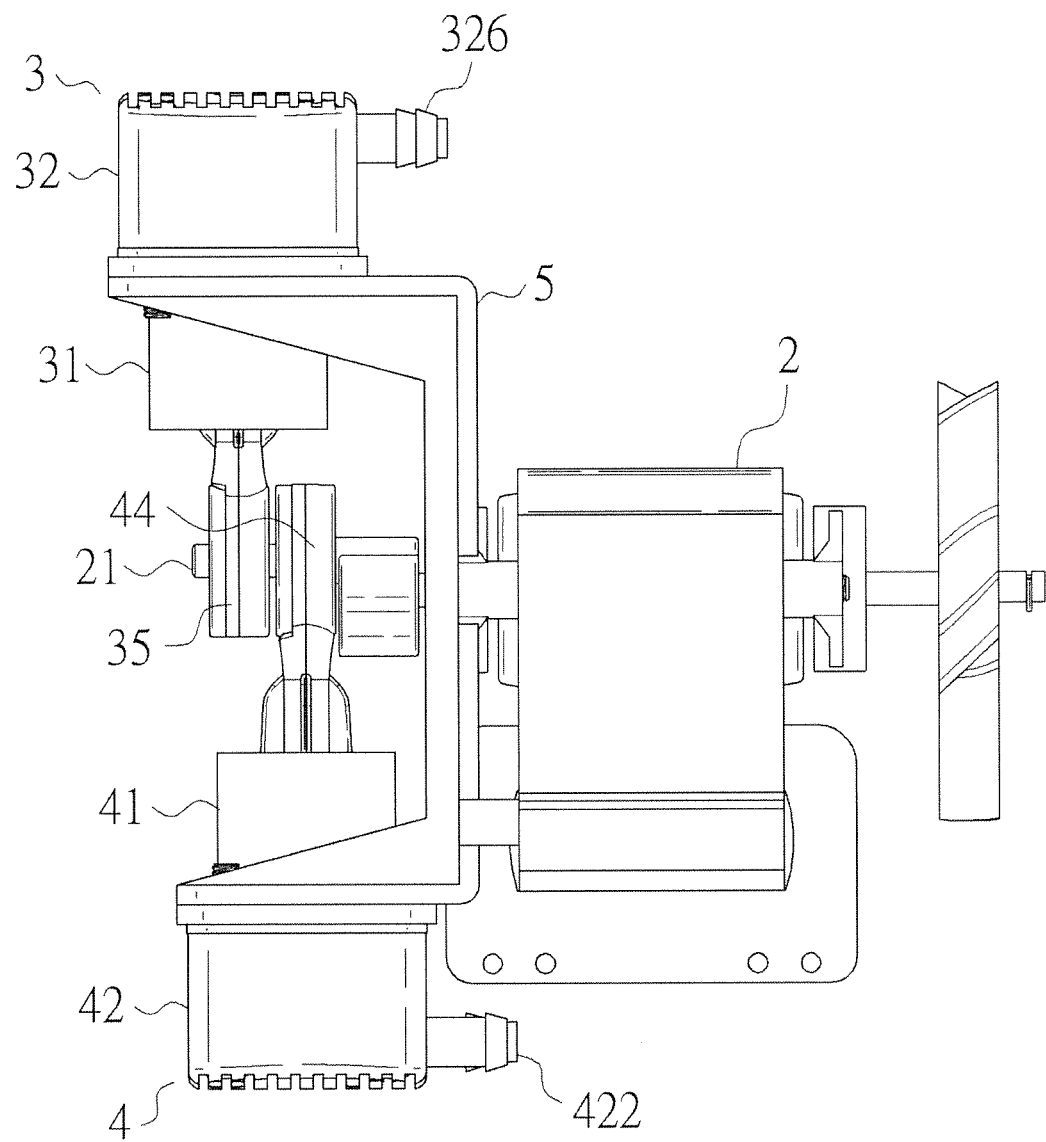
FIG. 5 is a side view of the dual cylinder structure of the atomizer of FIG. 3.
Figure 6:
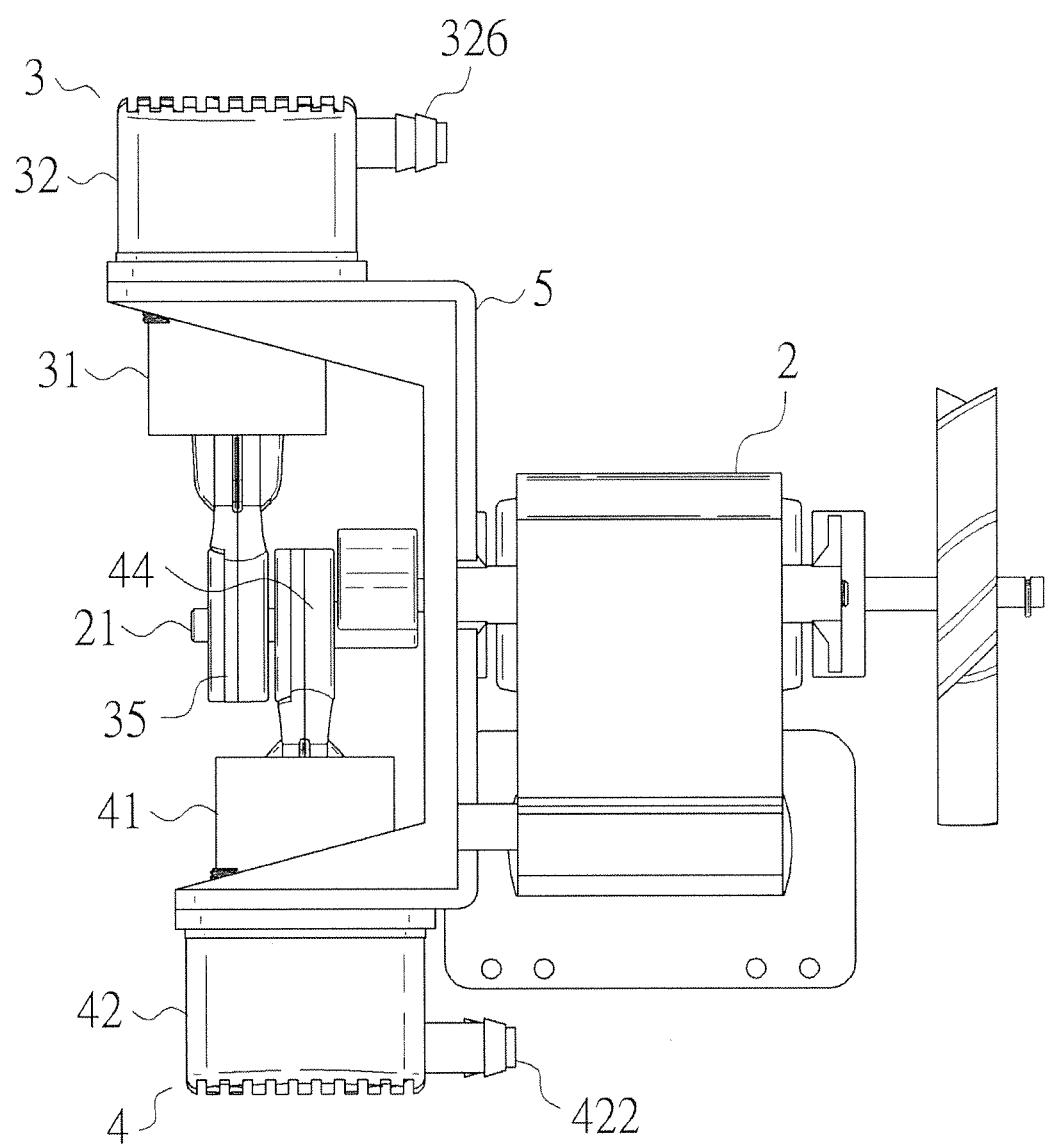
FIG. 6 is a view similar to FIG. 5, with pistons of the dual cylinder structure moved to another position.
Figure 7:
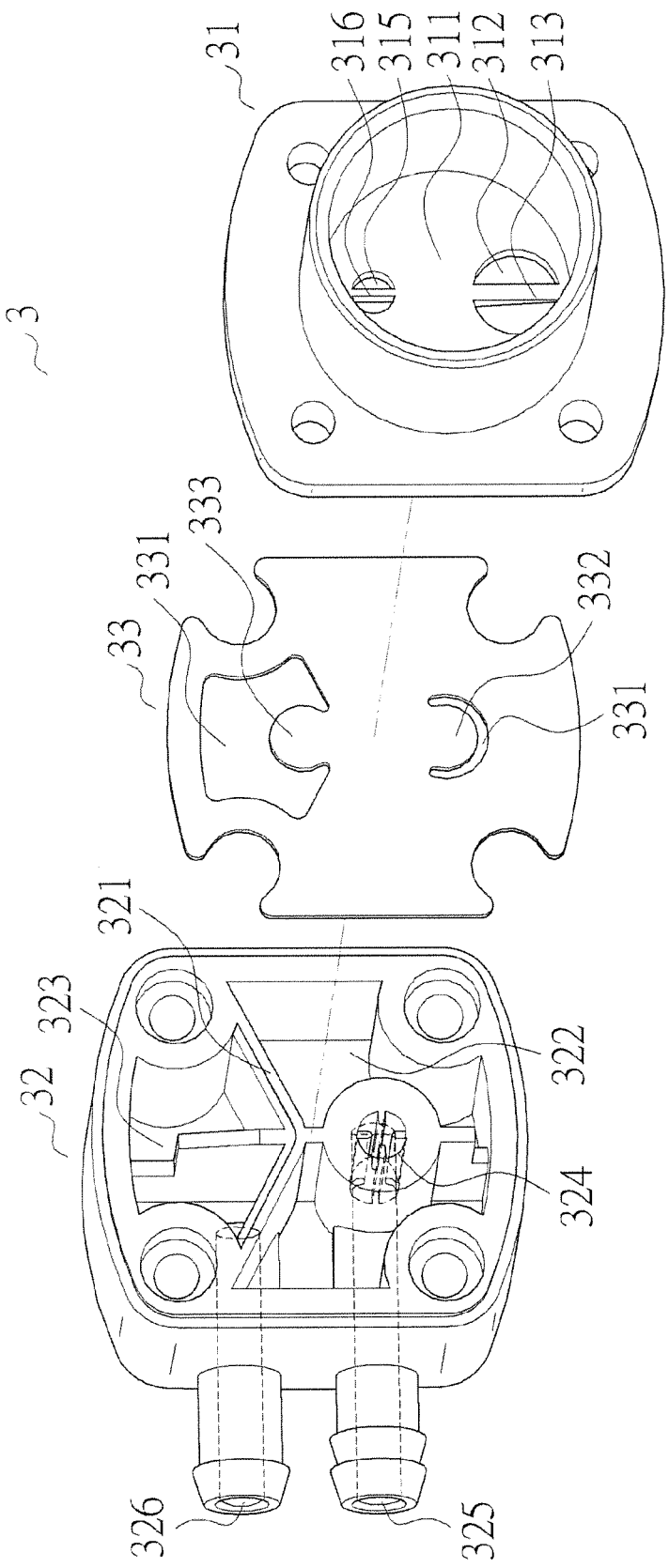
FIG. 7 is an exploded, perspective view of a cylinder unit of the dual cylinder structure according to the present invention.
Figure 8:
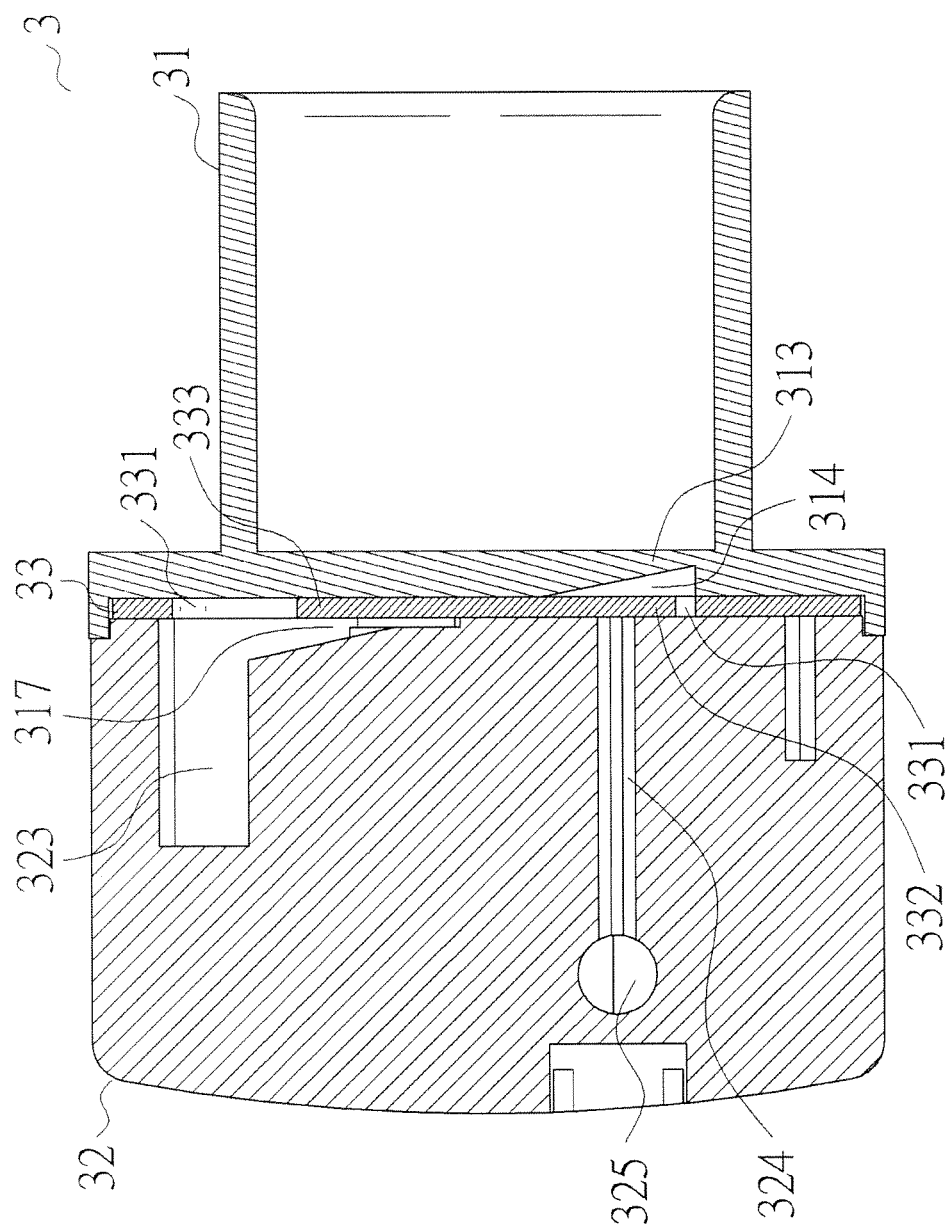
FIG. 8 is a cross sectional view of the cylinder unit of FIG. 7.

There are many cylinder units including the intake port 325, the outtake port 326, the inlet port 421, and the outlet port 422. FIGS. 4, 7, and 8 merely illustrate an example of the cylinder units and should not be construed in a limiting manner. In the form shown, each of the first and second cylinder units 3 and 4 includes a cylinder body 31, 41 and a cover 32, 42 covering the cylinder body 31, 41. The intake port 325 and the outtake port 326 of the first cylinder unit 3 are located in the cover 32 of the first cylinder unit 3. The inlet port 421 and the outlet port 422 of the second cylinder unit 4 are located in the cover 42 of the second cylinder unit 4.

The first and second cylinder units 3 and 4 are substantially identical to each other. Thus, description of the first cylinder unit 3 would be sufficient. In the form shown, the first cylinder unit 3 further includes a spacer plate 33 between the cylinder body 31 and the cover 32 of the first cylinder unit 3. The cylinder body 31 of the first cylinder unit 3 includes a top wall 311 facing the cover 32 of the first cylinder unit 3. The top wall 311 includes an inlet opening 312 and an outlet opening 315. The cover 32 of the first cylinder unit 3 includes an upper wall. A partitioning wall 321 extends from the upper wall of the cover 32 of the first cylinder unit 3 toward the cylinder body 31 of the first cylinder unit 3. The partitioning wall 321 has a bottom face pressing against the spacer plate 33. The upper wall of the cover 32 of the first cylinder unit 3, the partitioning wall 321, and the spacer plate 33 divide an interior of the cover 32 of the first cylinder unit 3 into an inlet section 322 and an outlet section 323 not in communication with the inlet section 322. The inlet opening 312 is in communication with the inlet section 322 and the intake port 325 of the cover 32 of the first cylinder unit 3 to form the intake passage of the first cylinder unit 3. The outlet opening 315 is in communication with the outlet section 323 and the outtake port 326 of the cover 32 of the first cylinder unit 3 to form the outtake passage of the first cylinder unit 3.

The spacer plate 33 includes a first punched hole 331 aligned with the inlet opening 312 of the cylinder body 31 of the first cylinder unit 3. The spacer plate 33 further includes a second punched hole 331 aligned with the outlet opening 315 of the cylinder body 31 of the first cylinder unit 3. A remaining material in the first punched hole 331 is connected to the spacer plate 33 and forms the intake check valve 332 of the first cylinder unit 3. A remaining material in the second punched hole 331 is connected to the spacer plate 33 and forms the outtake check valve 333 of the first cylinder unit 3.

The cover 32 of the first cylinder unit 3 includes a hollow tube 324 located in the inlet section 322 and extends toward the cylinder body 31 of the first cylinder unit 3. The hollow tube 324 is in communication with the inlet section 322 and the intake port 325 of the first cylinder unit 3. The hollow tube 324 has a bottom side pressing against the intake check valve 332 of the first cylinder unit 3.

The inlet opening 312 of the cylinder body 31 of the first cylinder unit 3 includes a first rib 313 extending in a diametric direction. The first rib 313 is spaced from the intake check valve 332 of the first cylinder unit 3 by a first spacing 314, providing room for the intake check valve 332. The intake check valve 332 of the first cylinder unit 3 has a free end capable of swinging toward the cylinder body 31 of the first cylinder unit 3 to open the intake passage of the first cylinder unit 3 such that an intake effect is provided when the piston 34 of the first cylinder unit 3 reciprocates.

The outlet opening 315 of the first cylinder unit 3 includes a second rib 316 extending in a diametric direction. The second rib 316 presses against the outtake check valve 333 of the first cylinder unit 3. The outtake check valve 333 of the first cylinder unit 3 is spaced from the outlet section 323 by a second spacing 317, providing room for the outtake check valve 333. The outtake check valve 333 of the first cylinder unit 3 has a free end capable of swinging toward the cover 32 of the first cylinder unit 3 such that an outtake effect is provided when the piston 34 of the first cylinder unit 3 reciprocates.

By providing room for the intake check valve 332, the outtake check valve 333 through the arrangement of the spacer plate 33, the intake check valve 332, the outtake check valve 33, the cover 32 and the cylinder body 31, various first and second cylinders 3 and 4 including the intake port 325, the outtake port 326, the inlet port 421, and the outlet port 422 can be used.

Although specific embodiments have been illustrated and described, numerous modifications and variations are still possible without departing from the scope of the invention. The scope of the invention is limited by the accompanying claims.

The invention claimed is:

1. An atomizer comprising:
a housing including an inlet, an outlet, a first vent and a second vent;
a motor mounted in the housing, with the motor including an eccentric transmission shaft;
a first cylinder unit mounted in the housing, with the first cylinder unit including a first piston and a first coupling bearing connected to the first piston, with the eccentric transmission shaft extending through the first coupling bearing, with the first piston moving reciprocatingly when the motor operates, with the first cylinder unit further including an intake port, with an intake check valve mounted in an intake flow path of the first cylinder unit, with the intake port of the first cylinder unit connected to an end of a first connection pipe, with the first connection pipe having another end connected to the inlet of the housing, forming an intake piping for the first cylinder unit, the first cylinder unit further including an outtake port, with an outtake check valve mounted in an outtake flow path of the first cylinder unit, with the outtake port of the first cylinder unit connected to an end of a third connection pipe, with the third connection pipe having another end connected to the first vent of the housing, forming an outtake piping for the first cylinder unit; and
a second cylinder unit mounted in the housing, with the second cylinder unit including a second piston and a second coupling bearing connected to the second piston, with the eccentric transmission shaft extending through the second coupling bearing, with the second piston moving reciprocatingly when the motor operates, with the second cylinder unit further including an outlet port, with an outlet check valve mounted in an outlet flow path of the second cylinder unit, with the outlet port of the second cylinder unit connected to an end of a second connection pipe, with the second connection pipe having another end connected to the outlet of the housing, forming an outlet piping for the second cylinder unit, the second cylinder unit further including an inlet port, with an inlet check valve mounted in an inlet flow path of the second cylinder unit, with the inlet port of the second cylinder unit connected to an end of a fourth connection pipe, with the fourth connection pipe having another end connected to the second vent of the housing, forming an inlet piping for the second cylinder unit.

2. The atomizer as claimed in claim 1, with the motor further including a mounting frame fixed to a side thereof, with the first and second cylinder units mounted to the mounting frame, with the eccentric transmission shaft located between the first and second cylinder units, with the first and second cylinder units spaced from each other by 180 degrees as viewed from a longitudinal axis of the eccentric transmission shaft.

3. The atomizer as claimed in claim 1, with each of the first and second cylinder units including a cylinder body and a cover covering the cylinder body, with the intake port and the outtake port of the first cylinder unit located in the cover of the first cylinder unit, with the inlet port and the outlet port of the second cylinder unit located in the cover of the second cylinder unit.

4. The atomizer as claimed in claim 3, with the first cylinder unit further including a spacer plate between the cylinder body and the cover of the first cylinder unit, the cylinder body of the first cylinder unit including a top wall facing the cover of the first cylinder unit, the top wall including an inlet opening and an outlet opening, the cover of the first cylinder unit including an upper wall, a partitioning wall extending from the upper wall of the cover of the first cylinder unit toward the cylinder body of the first cylinder unit, the partitioning wall having a bottom face pressing against the spacer plate, an interior of the cover of the first cylinder unit being formed between the upper wall of the cover of the first cylinder unit and the spacer plate, the partitioning wall dividing the interior of the cover of the first cylinder unit into an inlet section and an outlet section, the inlet section being isolated from fluid communication with the outlet section, with the inlet opening being in communication with the inlet section and the intake port of the cover of the first cylinder unit to form an intake passage for the intake flow path of the first cylinder unit, with the outlet opening being in communication with the outlet section and the outtake port of the cover of the first cylinder unit to form an outtake passage for the outtake flow path of the first cylinder unit, with the spacer plate including a first punched hole forming a first flap aligned with the inlet opening of the cylinder body of the first cylinder unit, with the spacer plate further including a second punched hole forming a second flap aligned with the outlet opening of the cylinder body of the first cylinder unit, with the first flap in the first punched hole connected to the spacer plate and forming the intake check valve of the first cylinder unit, with the second flap in the second punched hole connected to the spacer plate and forming the outtake check valve of the first cylinder unit, with the cover of the first cylinder unit including a hollow tube located in the inlet section and extending toward the cylinder body of the first cylinder unit, with the hollow tube being in communication with the inlet section and the intake port of the first cylinder unit, with the hollow tube having a bottom side pressing against the intake check valve of the first cylinder unit, with the inlet opening of the cylinder body of the first cylinder unit including a first rib extending in a diametric direction, with the first rib spaced from the intake check valve of the first cylinder unit by a first spacing, providing room for the intake check valve, with the intake check valve of the first cylinder unit having a free end capable of swinging toward the cylinder body of the first cylinder unit to open the intake passage of the first cylinder unit such that an intake effect is provided when the piston of the first cylinder unit reciprocates, with the outlet opening of the first cylinder unit including a second rib extending in a diametric direction, with the second rib pressing against the outtake check valve of the first cylinder unit, with the outtake check valve of the first cylinder unit spaced from the outlet section by a second spacing, providing room for the outtake check valve, with the outtake check valve of the first cylinder unit having a free end capable of swinging toward the cover of the first cylinder unit such that an outtake effect is provided when the piston of the first cylinder unit reciprocates.

* * * * *